United States Patent [19]

Hocquaux et al.

[11] Patent Number: 5,772,990
[45] Date of Patent: Jun. 30, 1998

[54] COMPOSITION FOR SLOWING DOWN THE LOSS OF HAIR BASED ON PYRIMIDINE N-OXIDES TRIAMINOSUBSTITUTED OR THEIR SULFOCONJUGATED

[75] Inventors: Michel Hocquaux, Paris; Khalid Bakkar, Sevran; Jean Baptiste Galey, Paris; Eric Terranova, Asnières, all of France

[73] Assignee: L'Oreal, Paris, France

[21] Appl. No.: 169,754

[22] Filed: Dec. 20, 1993

Related U.S. Application Data

[63] Continuation of Ser. No. 899,884, Jun. 17, 1992, abandoned.

[30] Foreign Application Priority Data

Jun. 20, 1991 [FR] France ................................. 91 07591

[51] Int. Cl.⁶ ................................ A61K 7/06; A61K 7/00
[52] U.S. Cl. ........................ 424/70.1; 514/256; 514/275; 514/880
[58] Field of Search .......................... 424/70.1; 514/256, 514/880

[56] References Cited

U.S. PATENT DOCUMENTS

| | | | |
|---|---|---|---|
| 4,287,338 | 9/1981 | McCall | 544/207 |
| 4,308,271 | 12/1981 | DeGeeter | 514/272 |
| 4,596,812 | 6/1986 | Chidsey | 514/256 |
| 4,945,093 | 7/1990 | Maignan | 514/235.8 |
| 4,968,685 | 11/1990 | Grollier | 514/256 |

FOREIGN PATENT DOCUMENTS

| | | |
|---|---|---|
| 0064012 | 11/1982 | European Pat. Off. . |
| 0211610 | 2/1987 | European Pat. Off. . |
| 0334586 | 9/1989 | European Pat. Off. . |
| 0375388 | 6/1990 | European Pat. Off. . |
| 0403238 | 12/1990 | European Pat. Off. . |
| 0420707 | 4/1991 | European Pat. Off. . |
| 1477048 | 4/1967 | France . |
| 2091516 | 1/1972 | France . |
| 2169787 | 9/1973 | France . |
| 2581542 | 11/1986 | France . |
| 8504577 | 10/1985 | WIPO . |
| 86/00616 | 1/1986 | WIPO . |
| 86/04231 | 7/1986 | WIPO . |

OTHER PUBLICATIONS

J. Med. Chem., 1983, 26, pp. 1791–1793.

*Primary Examiner*—Sally Gardner-Lane
*Attorney, Agent, or Firm*—Jacobson, Price, Holman & Stern, PLLC

[57] ABSTRACT

Composition for slowing down the loss of hair and for inducing and stimulating its growth, comprising a compound of formula:

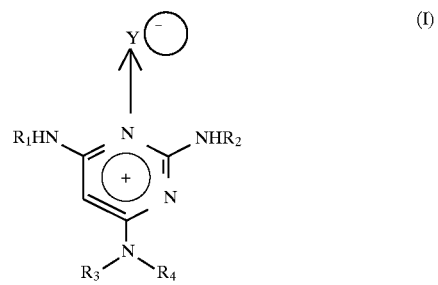

in which:

$R_1$ and $R_2$ denote H or an alkyl and do not simultaneously denote H;

$R_3$ and $R_4$ denote H, an alkyl or a heterocyclic ring with the nitrogen in position 6 and do not simultaneously denote H;

X denotes H or a halogen;

Y denotes O or $OSO_3$;

and their addition salts of physiologically acceptable acids.

13 Claims, No Drawings

COMPOSITION FOR SLOWING DOWN THE LOSS OF HAIR BASED ON PYRIMIDINE N-OXIDES TRIAMINOSUBSTITUTED OR THEIR SULFOCONJUGATED

This application is a continuation of application Ser. No. 07/899,884, filed Jun. 17, 1992, now abandoned.

BACKGROUND OF THE INVENTION

The invention relates to compositions intended to be employed, especially as topical application, for slowing down the loss of hair and for inducing and stimulating its growth, containing pyrimidine N-oxide compounds trisubstituted by an amine functional group in positions 2, 4 and 6, or their sulfoconjugated derivatives, and to the new pyrimidine N-oxide compounds or their sulfoconjugated derivatives employed in these compositions.

PRIOR ART 2,4-Diamino-6-piperidinopyrimidine 3-oxide or minoxidil is already known in the state of the art for its properties as an antihypertensive agent, but also for its use in the treatment of hair loss, of pelade, of desquamative dermatitis and of alopecia.

SUMMARY OF THE INVENTION

The Applicant has found new compositions for the treatment and the prevention of hair loss, which are employed especially as topical application, and are particularly effective in the treatment of diseases of the scalp by virtue of a particular class of compounds derived from pyrimidine 3-oxide which are trisubstituted by an amine functional group in positions 2, 4 and 6.

The compounds chosen by the Applicant are particularly effective for the regrowth of hair and for inducing and stimulating its growth and slowing down its loss. In addition, they exhibit an excellent solubility in the media which are usually employed in cosmetics and in pharmacy.

Moreover, the Applicant has found that some of these derivatives exhibit an antihypertensive activity which is markedly lower than that of minoxidil, or even none.

The subject of the invention is therefore new compositions for the treatment and the prevention of hair loss, containing pyrimidine N-oxide compounds or their individual sulfoconjugated derivatives.

A further subject of the invention is new pyrimidine N-oxide compounds or their sulfoconjugated derivatives employed in these compositions.

Another subject relates to the use of the compounds of the invention for the preparation of a medication for the treatment of hair loss.

Other subjects will appear in the light of the description and the examples which follow.

DETAILED DESCRIPTION

The compositions in accordance with the invention are essentially those which contain, in a physiologically acceptable medium, at least one compound of the following formula:

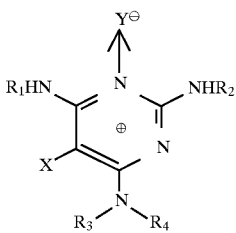

(I)

in which $R_1$ and $R_2$, independently of each other, denote a hydrogen atom or a $C_1$–$C_8$ alkyl radical, on condition that they do not simultaneously denote a hydrogen atom;

$R_3$ and $R_4$, independently of each other, denote a hydrogen atom or a $C_1$–$C_8$ alkyl radical or form, with the nitrogen atom attached to position 6 of the pyrimidine ring, a $C_{3-C8}$ heterocyclic ring, on condition that they do not simultaneously denote a hydrogen atom;

X denotes a hydrogen atom or a halogen;

Y denotes O or $OSO_3$.

The compounds of formula (I), in accordance with the invention, can be converted into their addition salts of cosmetically or pharmaceutically acceptable acids, such as the salts of sulfuric, hydrochloric, hydrobromic, phosphoric, acetic, benzoic, salicylic, glycolic, succinic, nicotinic, tartaric, maleic, pamoic, methanesulfonic, picric, lactic and similar acids.

In accordance with the invention the $C_1$–$C_8$ alkyl radicals are preferably chosen from methyl, ethyl, n-propyl, isopropyl, n-butyl, tert-butyl, octyl, 2-ethyl-hexyl and hexyl radicals.

A halogen atom means preferably chlorine or bromine.

A $C_3$–$C_8$ heterocyclic group means preferably the morpholino, piperidino, pyrrolidino, piperazino and N-4'-alkylpiperazino groups in which the alkyl group in position 4' contains preferably 1 to 6 carbon atoms.

Among the compounds of general formula (I), a number of compounds are known per se and have been described as antihypertensive agents, especially in patents U.S. Pat. No. 4,287,338 and U.S. Pat. No. 4,308,271 (Upjohn).

The new compounds in accordance with the present invention have the structure:

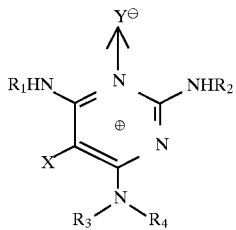

(I')

in which $R_1$, $R_2$, $R_3$, $R_4$ and X have the same meanings shown in formula (I) above, provided that $R_1$ and $R_2$ simultaneously denote a $C_1$–$C_8$ alkyl radical; and their addition salts of physiologically acceptable acids.

The individual compounds of the following formula (IA):

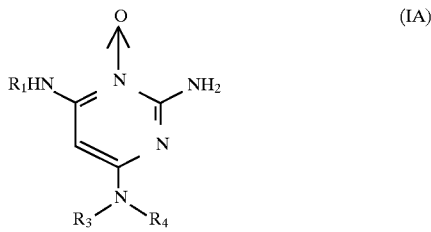

in which $R_1$, $R_3$ and $R_4$ have the same abovementioned meanings can be obtained by reacting an amine of formula $R_1NH_2$ with 2-amino-4,6-dichloropyrimidine of formula:

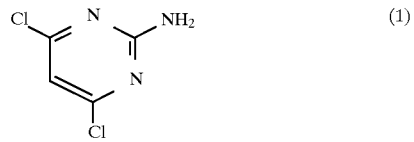

An oxidation in position 3 of the pyrimidine nucleus is then performed with a carboxylic peracid such as metachloroperbenzoic acid, followed by the introduction of the amine $NHR_3R_4$ by aromatic nucleophilic substitution onto the pyrimidine nucleus of the product obtained.

This process can be represented by the following scheme:

SCHEME A

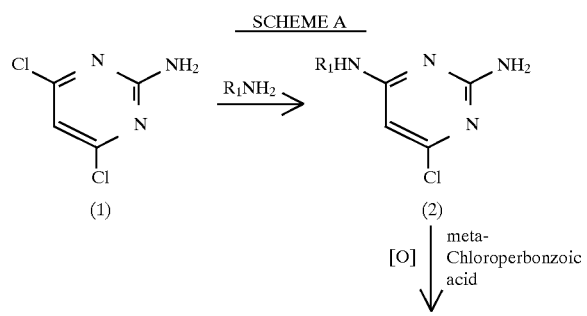

-continued
SCHEME A

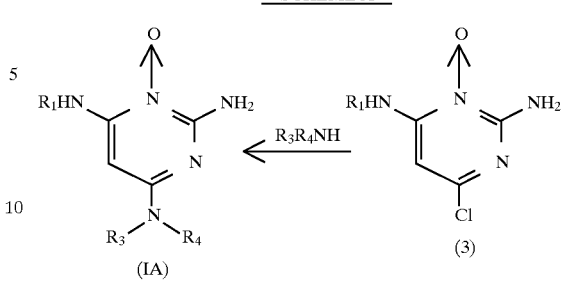

The individual compounds of following formula (IB):

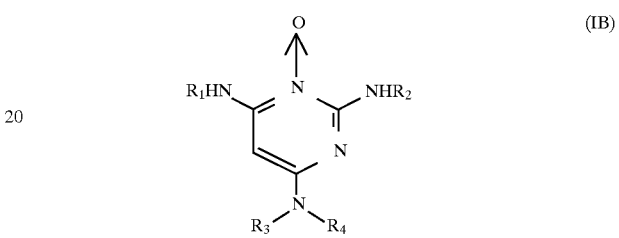

in which $R_1$, $R_2$, $R_3$ and $R_4$ have the same abovementioned definitions are obtained by reacting an amine $R_1NH_2$ and an amine $R_2NH_2$ successively with 2,4,6-trichloropyrimidine of formula (4):

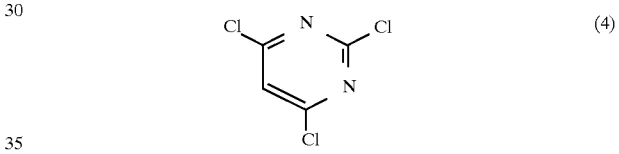

An oxidation in position 3 of the pyrimidine nucleus is then performed with a carboxylic peracid, preferably meta-chloroperbenzoic acid, followed by an aromatic nucleophilic substitution of the chlorine atom in position 6 by an amine $HNR_3R_4$.

This process can be represented by the following scheme:

SCHEME B

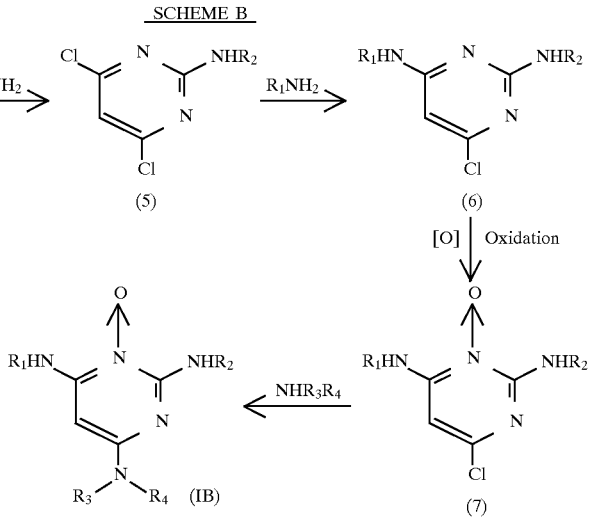

The individual compounds of following formula (IC):

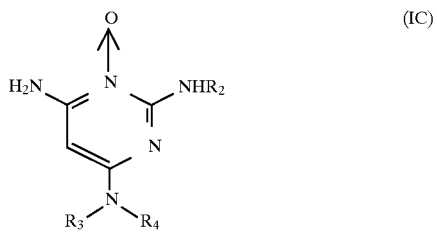

in which $R_1$, $R_2$, $R_3$ and $R_4$ have the same abovementioned meanings are obtained by reacting Oxone® ($KHSO_5$) with 2-thiomethyl-6-chloro-4-aminopyrimidine of formula:

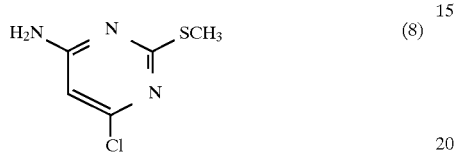

An amino-$NHR_2$ substituent is introduced in position 2 of the pyrimidine nucleus of the product (9) obtained. An oxidation in position 3 of the pyrimidine nucleus is then performed with the aid of a carboxylic peracid, preferably meta-chloroperbenzoic acid, followed by the introduction of the amine $NHR_3R_4$ in position 6 by aromatic nucleophilic substitution.

This process can be represented by the following schemes:

SCHEME C

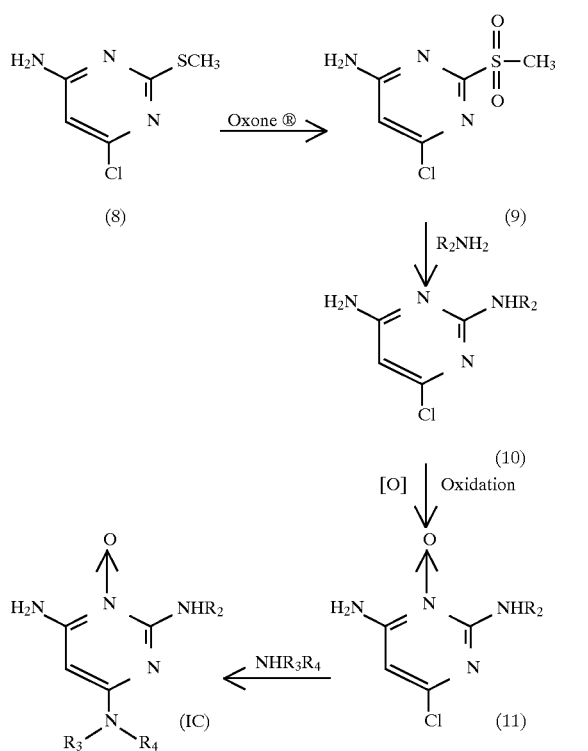

The individual compounds of the invention of general formula (I) in which Y denotes an oxygen atom can be converted into their O-sulfate homologs, of formula (ID) defined above, by chemical sulfating according to the conventional methods described in the literature (J. Med. Chem., 1983, 26, pages 1791–1793).

Sulfur trioxide-pyridine, sulfur trioxide-tri-ethylamine or sulfur trioxide-ethyldiisopropylamine complexes are employed as sulfating reactant.

The solvents employed are preferably dimethyl-formamide, chloroform, acetonitrile or their binary mixtures. The temperature is of the order of 0° to 25° C. and the reaction time varies from 1 to 24 hours.

SCHEME D

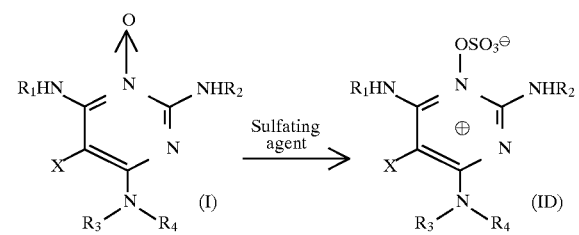

The individual compounds of following formula:

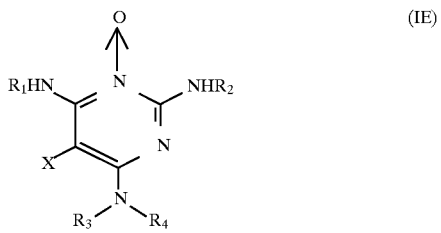

in which $R_1$, $R_2 R_3$ and $R_4$ have the same abovementioned meanings and X denotes a halogen are obtained from the above compounds (IA), (IB) and (IC) by reaction with an N-halosuccinimide of formula:

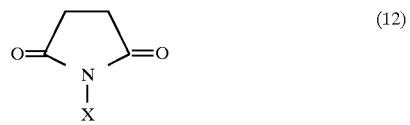

in the presence of an alcohol such as methanol.

The compositions in accordance with the present invention, containing, in a physiologically acceptable medium, at least one compound corresponding to the formula (I) or one of its addition salts of physiologically acceptable acids can be applied in the cosmetic or pharmaceutical field, especially by topical application. They are intended for the treatment and prevention of hair loss and especially of pelade, of alopecia and of desquamative dermatitis.

As a physiologically acceptable medium, these compositions may include any medium which is appropriate for topical application either in cosmetics or pharmacy and which is compatible with the active substance.

The compounds in accordance with the invention may be present in this medium either in the dissolved state or in the dispersed state, especially in micronized form.

The compositions intended to be employed in pharmacy are in the form of ointment, tincture, cream, pomade, powder, plaster, saturated pad, solution, emulsion or vesicular dispersion, lotion, gel, spray or suspension. They may be either anhydrous or aqueous, depending on the clinical indication.

The compounds according to the invention are present in these pharmaceutical compositions in concentrations between 0.1 and 10% by weight, and in particular of between 0.2 and 5% by weight.

The cosmetic compositions are especially intended to be employed in the form of a lotion, gel, soap, shampoo, aerosol or foam and contain, in a cosmetically acceptable carrier, at least one compound of formula (I) or one of its addition salts of acids.

The concentration of these compounds of formula (I) in these compositions is preferably between 0.01 and 5% by weight and in particular between 0.05 and 3% by weight.

The compositions in accordance with the invention may contain various additives usually employed in cosmetics or in pharmacy and in particular active substances such as hydrating agents like thiamorpholinone and its derivatives or urea, antiseborrheic agents such as S-carboxymethylcystein, S-benzylcysteamine and their derivatives, and thioxolone.

The compounds in accordance with the invention may be used in combination with compounds which further improve their activity on the regrowth and/or on the slowing down of the loss of hair, such as more particularly the following compounds:

nicotinic acid esters, including more particularly $C_1$–$C_6$ alkyl nicotinates and especially methyl or hexyl nicotinate, tocopherol or benzyl nicotinate;

steroidal and nonsteroidal antiinflammatory agents which are well known in the state of the art and in particular hydrocortisone, its salts and its derivatives and niflumic acid;

retinoids and more particularly t-trans-retinoic acid also known as tretinoin, isotretinoin, retinol or vitamin A and its derivatives such as the acetate, the palmitate or the propionate, motretinide, etretinate and zinc t-trans-retinoate;

antibacterial agents chosen more particularly from macrolides, pyranosides and tetracyclines and especially erythromycin;

calcium antagonist agents such as cinnarizine and diltiazem;

hormones such as estriol and analogs or thyroxin and its salts;

antiandrogenic agents such as oxendolone, spironolactone and diethylstilbestrol;

OH radical scavengers, such as dimethyl sulfoxide;

esterified oligosaccharides such as those described in EP-A-0,211,610 and EP-A-0,064,012;

hexosaccharic acid derivatives such as those described in EP-A-0,375,388, in particular glucosaccharic acid;

glycosidase inhibitors such as those described in EP-A-0,334,586, in particular D-glucaro-1,5-lactam;

glycosaminoglycanase and proteoglycanase inhibitors, such as those mentioned in EP-A-0,277,428, in particular L-galactono-1,4-lactone;

tyrosine kinase inhibitors such as those described in EP-A-0,403,238, in particular 1-amido-1-cyano-(3,4-dihydroxyphenyl)ethylene.

The compounds of the invention, optionally mixed with others, may also be used in combination with compounds such as diazoxide corresponding to 3-methyl-7-chloro-1,2,4[2H]benzothiadiazine 1,1-dioxide, spiroxazone or 7-(acetylthio)-4',5'-dihydrospiro-3-[androst-4-ene-17,2'-(3'H)furan]one, phospholipids such as lecithin, linoleic and linolenic acids, salicylic acid and its derivatives described more particularly in French Patent No. 2,581,542 and more particularly the salicylic acid derivatives bearing an alkanoyl group containing 2 to 12 carbon atoms in position 5 of the benzene ring, hydroxy-carboxylic or ketocarboxylic acids and their esters, lactones and their corresponding salts, anthralin, carotenoids and 5,8,11,14-eicosatetraynoic or 5,8,11-eicosatriynoic acids, their esters and amides.

The compounds in accordance with the invention can also be used in combination with surface-active agents including those chosen from nonionic and ampho-teric surface-active agents.

Among the nonionic surfactants there will be mentioned the polyhydroxypropyl ethers described especially in French Patent Nos. 1,477,048, 2,091,516, 2,169,787, 2,328,763 and 2,574,786, oxyethylenated $C_8$–$C_9$-alkylphenols containing from 1 to 100 moles of ethylene oxide and preferably 5 to 35 moles of ethylene oxide, alkylpolyglycosides of formula:

$$C_nH_{2n+1}(C_6H_{10}O_5)_xH \qquad (A)$$

in which n varies from 8 to 15 inclusive and x from 1 to 10 inclusive.

Among the amphoteric surface-active agents there will be mentioned the amphocarboxyglycinates and the amphocarboxypropionates defined in the CTFA dictionary, 3rd edition, 1982, and sold, in particular, under the name Miranol® by the Miranol company.

The compounds according to the invention may be introduced in carriers which further improve the activity in respect of the regrowth, at the same time exhibiting properties which are advantageous from a cosmetic view-point, such as ternary volatile mixtures of alkylene glycol alkyl ethers, in particular of $C_1$–$C_4$ alkyl, of $C_1$–$C_4$ alkylene glycol or of dialkylene glycols, preferably of $C_1$–$C_4$ dialkylene glycol, ethyl alcohol and water, the glycolic solvent denoting ethylene glycol monoethyl ethers, propylene glycol monomethyl ether and diethylene glycol monomethyl ether.

The compounds in accordance with the invention can also be introduced in gelled or thickened physiologically acceptable carriers such as essentially aqueous carriers gelled with heterobiopolysaccharides, such as xanthan gum, scleroglucans, or cellulose derivatives such as cellulose ethers, hydroalcoholic carriers gelled with polyhydroxyethyl acrylates or methacrylates or essentially aqueous carriers thickened in particular with poly-acrylic acids crosslinked with a polyfunctional agent, such as the Carbopols sold by the Goodrich company.

These compositions may also contain preserving agents, stabilizers, pH-regulators, osmotic pressure modifiers, emulsifiers, UV-A and UV-B filters, antioxidants such as a-tocopherol, butylhydroxyanisole and butylhydroxytoluene.

The physiologically acceptable medium may consist of water or of a mixture of water and of a solvent or a mixture of solvents, the solvents being chosen from organic solvents which are acceptable from the cosmetic or pharmaceutical viewpoint and which are chosen more particularly from $C_1$–$C_4$ lower alcohols like ethyl alcohol, isopropyl alcohol, tert-butyl alcohol, alkylene glycols and their alkyl ethers referred to above.

The solvents, when present, are present in proportions of between 1 and 80% by weight, relative to the total weight of the composition.

The thickeners are preferably present in proportions of between 0.1 and 5% by weight and in particular between 0.4 and 3% by weight relative to the total weight of the composition.

A further subject of the invention is a process for cosmetic treatment of hair or of the scalp, consisting in applying thereto at least one composition as defined above, with a view to improving the esthetics of the head of hair.

Another subject of the invention consists of the use of the composition containing the compounds of formula (I)

defined above, for the preparation of a medication whose effect is to induce or to stimulate the growth of hair and to slow down its loss.

The treatment consists essentially in applying the composition as defined above to the alopecic regions of the scalp of an individual.

The preferred method of application consists in applying 1 to 2 g of the composition to the alopecic region, with a frequency of one to two applications daily, for 1 to 7 days per week, this being done for a period of 1 to 6 months.

The compositions may in particular be employed in the treatment of pelade, of hair loss, of desquamative dermatitis or of alopecia.

The following examples are intended to illustrate the invention without, however, being limiting in nature.

EXAMPLES OF PREPARATION

Example 1
2-Amino-4-propylamino-6-dimethylaminopyrimidine 3-oxide

The product is prepared according to the reaction scheme:

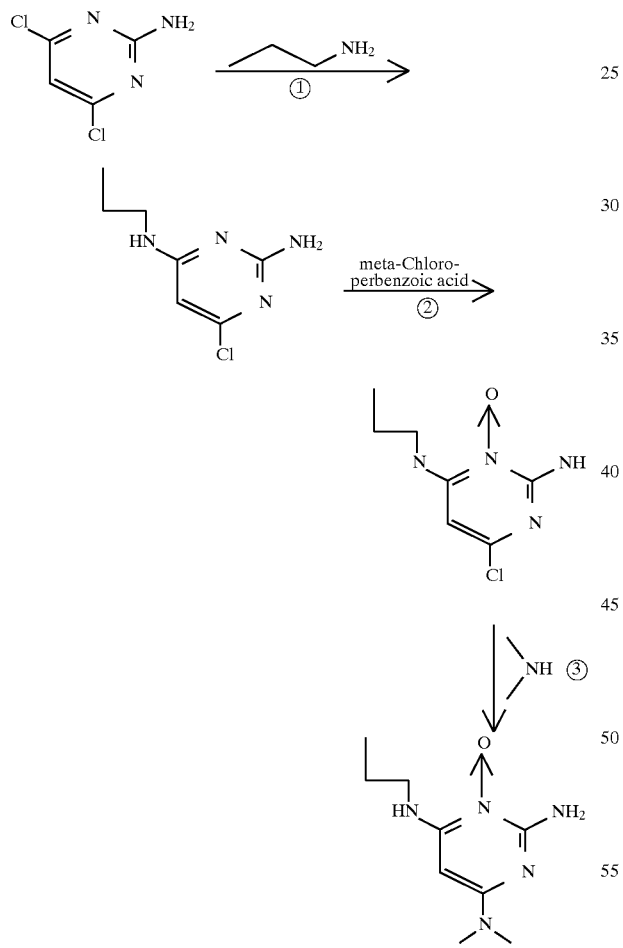

Stage 1

10 g of 2-amino-4,6-dichloropyrimidine are dispersed in 100 ml of methanol and 10 ml of propylamine are then added and the mixture is refluxed for 24 hours.

The mixture is concentrated and 100 ml of water are then added. The precipitate is filtered off cold and then recrystallized from acetonitrile.

The white solid isolated is dried to obtain 6.3 g of 2-amino-4-propylamino-6-chloropyrimidine.

Yield=55%

M.p.=104° C.

The $^1$H and $^{13}$C NMR and mass spectra are consistent with the expected structure.

| Elemental analysis for $C_7H_{11}N_4Cl$ | | | | |
|---|---|---|---|---|
| | C | H | N | Cl |
| Calculated | 45.05 | 5.94 | 30.02 | 18.99 |
| Found | 45.13 | 5.98 | 30.14 | 18.87 |

Stage 2

18 g of meta-chloroperbenzoic acid are added to a solution of 5 g of 2-amino-4-propylamino-6-chloro-pyrimidine in 100 ml of ethanol at 0° C.

This mixture is stirred at 0° C. for 6 hours and is then filtered and 2.4 g of 2-amino-4-propylamino-6-chloropyrimidine 3-oxide are recovered.

Yield=44%

M.p.=190°–195° C.

The $^1$H and $^{13}$C NMR and mass spectra are consistent with the expected structure.

Stage 3

2 g of 2-amino-4-propylamino-6-chloropyrimidine 3-oxide are dispersed in 50 ml of solution of dimethyl-amine at a concentration of 33% in ethanol.

The mixture is refluxed for 3 hours.

The reaction mixture is evaporated under vacuum.

The oil obtained is treated with 20 ml of hydro-chloric ethanol.

The hydrochloride obtained is filtered off and rinsed with ether.

The solid is treated with alcoholic potassium hydroxide and is then filtered off on Celite and the filtrate is evaporated under vacuum. The residue is then recrystallized from 50 ml of acetone plus 3 ml of water. 0.77 g of 2-amino-4-propylamino-6-dimethylaminopyrimidine 3-oxide are recovered.

Yield=37%

M.p.=217°–218° C.

The $^1$H and $^{13}$C NMR and mass spectra are consistent with the expected structure.

| Elemental analysis for $C_9H_{17}N_5O$ | | | | |
|---|---|---|---|---|
| | C | H | N | O |
| Calculated | 51.17 | 8.11 | 33.15 | 7.57 |
| Found | 51.24 | 8.15 | 33.23 | 7.70 |

Example 2

2-Amino-4-isopropylamino-6-dimethylaminopyrimidine 3-oxide

The product is prepared according to the reaction scheme:

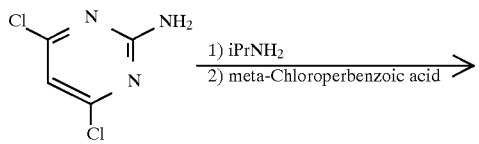

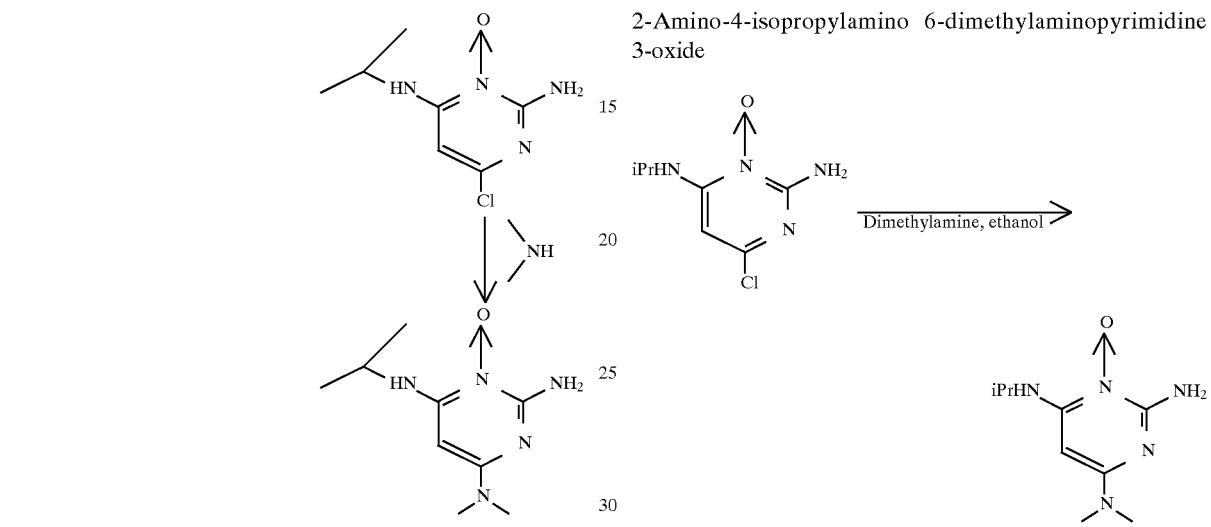

Stage 1
2-Amino-4-isopropylamino-6-chloropyrimidine 3-oxide

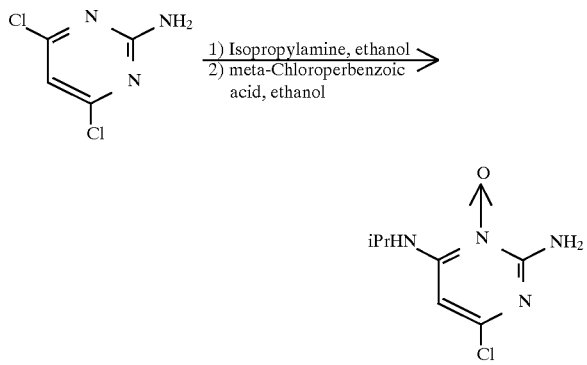

10 g of 2-amino-4,6-dichloropyrimidine are suspended in 100 ml of ethanol. 18 g of isopropylamine are added. The reaction mixture is refluxed for 6 hours. It is evaporated to dryness and then taken up in 50 ml of water. After 1 hour's stirring the precipitate is filtered off on sintered glass and then dried under vacuum over phosphorus pentoxide.

The precipitate obtained is placed in 300 ml of ethanol. 28.70 g of meta-chloroperbenzoic acid are added using little spatulas. The reaction mixture is stirred at room temperature for 6 hours. 100 ml of water are added and the ethanol is then evaporated off. The pH of the reaction mixture is then adjusted to 1 by adding concentrated hydrochloric acid. After 1 hour's stirring the precipitate is filtered off on sintered glass, rinsed with 50 ml of water and discarded. The filtrates are adjusted to pH=8 by adding sodium hydroxide. They are extracted with 2×100 ml of dichloromethane. The organic phase is dried over sodium sulfate, filtered on paper and evaporated to dryness. The precipitate is taken up in 50 ml of ethyl ether, stirred for 1 hour and filtered off on sintered glass. 4.05 g of 2-amino-4-isopropyl-amino-6-chloropyrimidine 3-oxide are obtained.

Yield=33%.

The $^1$H NMR and mass spectra are consistent with the expected structure.

Stage 2
2-Amino-4-isopropylamino 6-dimethylaminopyrimidine 3-oxide

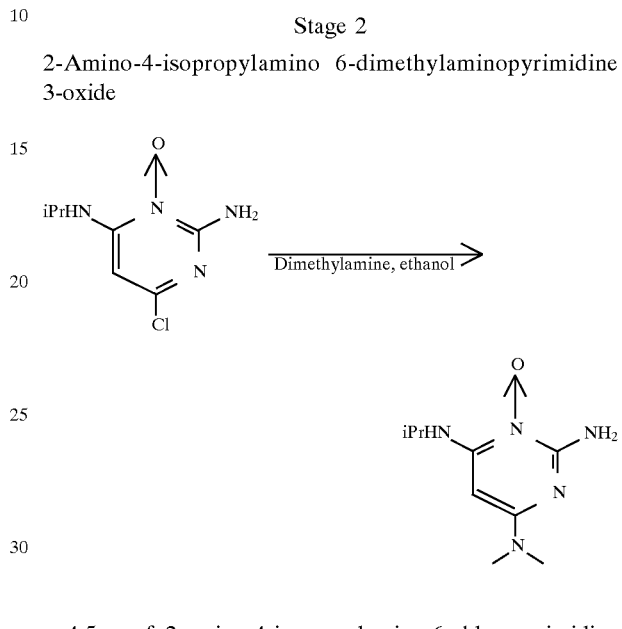

4.5 g of 2-amino-4-isopropylamino-6-chloropyrimidine 3-oxide are placed in 25 ml of ethanol. 20 ml of dimethylamine in solution at a concentration of 33% in ethanol are added. The reaction mixture is refluxed for 2 h 30 minutes and then evaporated to dryness. The precipitate is dissolved in 10 ml of ethanol. Hydrochloric ethanol is added to pH=1. After stirring for 1 hour, 20 ml of ethyl ether are added. The precipitate is filtered off on sintered glass, rinsed with 20 ml of ethyl ether and dried under vacuum.

The precipitate is taken up in 20 ml of water. The pH is adjusted to 8 by adding sodium hydroxide. After 1 hour's stirring the precipitate is filtered off on sintered glass. It is recrystallized from 55 ml of acetonitrile-water (9/1). 2.55 g of 2-amino-4-isopropyl-amino-6-dimethylaminopyrimidine 3-oxide are obtained.

Yield=56%.

| Elemental analysis for $C_9H_{17}N_5O$; M = 211 | | | | |
| --- | --- | --- | --- | --- |
|  | C | H | N | O |
| Calculated | 51.18 | 8.06 | 33.17 | 7.58 |
| Found | 51.15 | 8.07 | 33.11 | 7.74 |

The $^1$H NMR and mass spectra are consistent with the expected structure.

Example 3

2,4-N,N'-Dipropylamino-6-dimethylaminopyrimidine 3-oxide

The product is prepared according to the following reaction scheme:

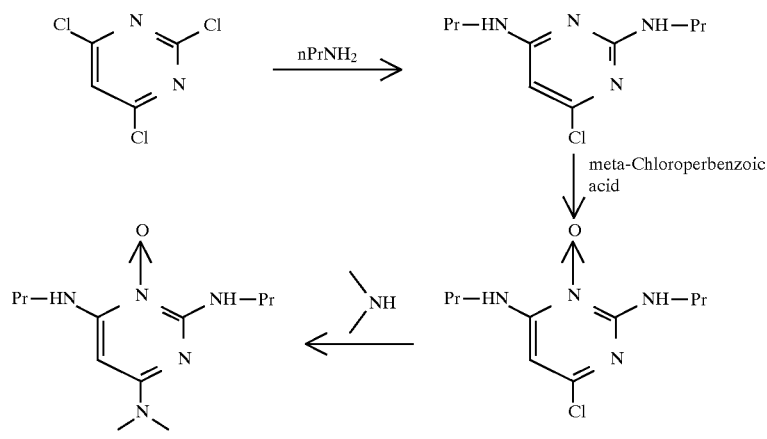

Stage 1

2,4-N,N'-Dipropylamino-6-chloropyrimidine

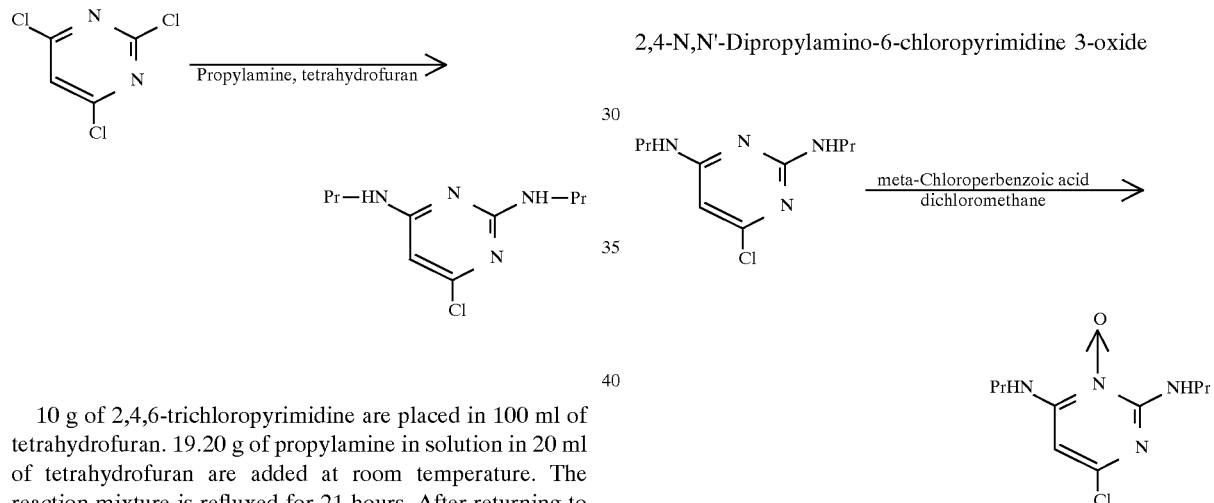

Stage 2

2,4-N,N'-Dipropylamino-6-chloropyrimidine 3-oxide 10 g of 2,4,6-trichloropyrimidine are placed in 100 ml of tetrahydrofuran. 19.20 g of propylamine in solution in 20 ml of tetrahydrofuran are added at room temperature. The reaction mixture is refluxed for 21 hours. After returning to room temperature it is washed with 100 ml of water. The aqueous phase is extracted with 10 ml of dichloromethane. The organic phases are combined, dried over sodium sulfate, filtered on paper and evaporated to dryness. The oil obtained is purified by chromatography on a silica column (eluent: dichloromethane). 10.75 g of 2,4-N,N'-dipropylamino-6-chloropyrimidine are obtained.

Yield=86%.

| Elemental analysis for $C_{10}H_{17}N_4Cl$; M = 228.5 | | | | |
|---|---|---|---|---|
| | C | H | N | Cl |
| Calculated | 52.51 | 7.44 | 24.50 | 15.54 |
| Found | 52.53 | 7.40 | 24.60 | 15.54 |

The $^1H$ NMR and mass spectra are consistent with the expected structure.

6.35 g of 2,4-N,N'-dipropylamino-6-chloropyrimidine are placed in 200 ml of dichloromethane. 21.80 g of meta-chloroperbenzoic acid are added using little spatulas. The reaction mixture is stirred at room temperature for 4 hours. It is evaporated to dryness. The residue is taken up in 200 ml of water. The pH is adjusted to 8 by adding sodium hydroxide. The mixture is extracted with 3×100 ml of dichloromethane. The organic phase is dried over sodium sulfate, filtered on paper and evaporated to dryness. The oil obtained is purified by chromatography on a silica column (eluents: ethyl acetate/methanol with a polarity gradient of 0 to 5% of methanol). 620 mg of 2,4-N,N'-dipropylamino-6-chloropyrimidine 3-oxide are obtained.

Yield: 9%

The $^1H$ NMR and mass spectra are consistent with the expected structure.

Stage 3

2,4-N,N'-Dipropylamino-6-dimethylaminopyrimidine 3-oxide

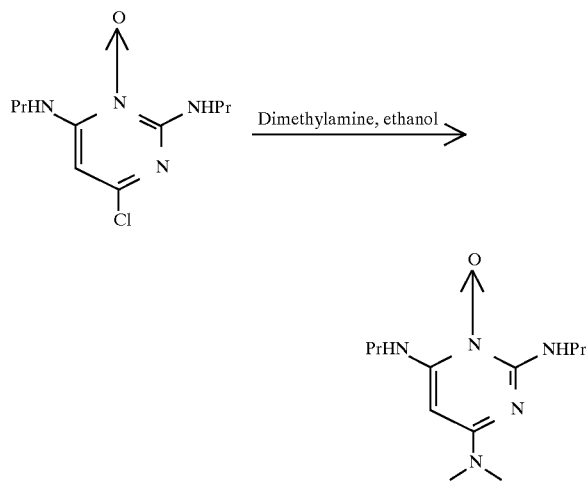

620 mg of 2,4-N,N'-dipropylamino-6-chloropyrimidine 3-oxide are placed in 15 ml of ethanol. 1 ml of dimethylamine is added as a solution at a concentration of 33% in ethanol. The reaction mixture is refluxed for 7 h 30 minutes and then evaporated to dryness. The residue is taken up in 10 ml of ethyl ether. Chlorohydric ethanol is added to an acidic pH. After 1 hour's stirring the solution is filtered on sintered glass. The precipitate is taken up in 5 ml of water. The pH is adjusted to 8 by adding sodium hydroxide. After 1 hour's stirring the mixture is filtered on sintered glass. The precipitate is recrystallized from 3 ml of acetone. 120 mg of 2,4-N,N'-dipropylamino-6-dimethylaminopyrimidine 3-oxide are obtained.

Yield=19%.

| Elemental analysis for $C_{12}H_{23}N_5O$; M = 253 | | | |
|---|---|---|---|
| | C | H | N | O |
| Calculated | 56.92 | 9.09 | 27.67 | 6.32 |
| Found | 57.04 | 9.13 | 27.85 | 6.38 |

The $^1$H NMR and mass spectra are consistent with the expected structure.

Example 4

Synthesis of 2-propylamino-4-amino-6-N,N-dimethylamino-6-pyrimidine 3-oxide

Stage 1

2-Methylsulfonyl-4-amino-6-chloropyrimidine

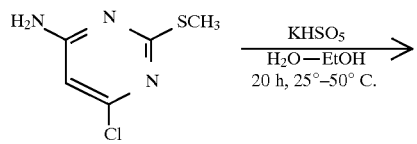

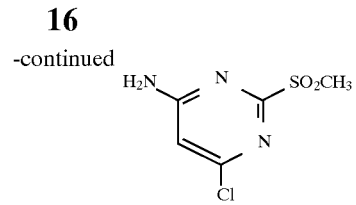

Procedure 13.17 g of 2-thiomethyl-4-amino-6-chloropyrimidine in solution in 400 ml of ethanol are introduced into a 1-liter three-necked round bottom flask. This solution is cooled to about +4° C. and 69.14 g of Oxone® in solution in 300 ml of water are then added. The reaction mixture becomes heterogeneous. It is stirred vigorously. After 16 hours' reaction at 25° C. the reaction is heated slightly to about 50° C. for another 4 hours. The mixture is then cooled between 5° and 10° C. and then filtered. The precipitate obtained is taken up with stirring in 300 ml of water for a first time and is then filtered. It is taken up as before in 100 ml of water. After filtering and draining, the product is dried in vacuum and over $P_2O_5$ at 70° C. overnight. 10.85 g of 2-methylsulfonyl-4-amino-6-chloropyrimidine are obtained in the form of a white powder.

Yield=83%

M.p.=239° C.

| Elemental analysis for $C_5H_6ClN_3O_2S$; M = 207.64 | | | | | |
|---|---|---|---|---|---|
| | C | H | Cl | N | O | S |
| Calculated | 28.92 | 2.89 | 17.11 | 20.24 | 15.42 | 15.42 |
| Found | 29.10 | 2.95 | 16.98 | 20.12 | 15.59 | 15.40 |

The $^1$H NMR and mass spectra are consistent with the expected structure.

Stage 2

2-n-Propylamine-4-amino-6-chloropyrimidine

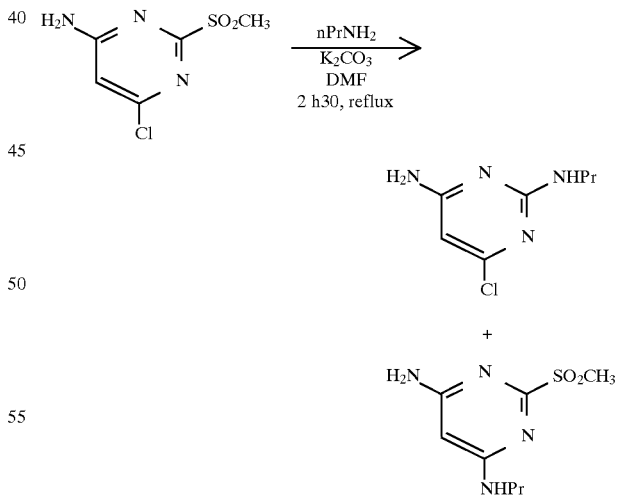

6.04 g of 2-methylsulfonyl-4-amino-6-chloro-pyrimidine in 150 ml of DMF are introduced into a 250-ml three-necked flask fitted with a thermometer and a reflux condenser, followed by 2.56 g of n-propylamine and 3 g of $K_2CO_3$. The reaction is heated until DMF refluxes for 2 h 30 minutes.

The solvent is evaporated off under vacuum and the liquid product obtained is taken up in 100 ml of water. This aqueous phase is extracted with 5×50 ml of diethyl ether.

The ether phases are combined, dried over Na₂SO₄ and the solvent is evaporated off. 5.4 g of very viscous liquid crude product are collected. This crude product is chromatographed on a silica column [eluent: CH₂Cl₂/CH₃OH(98/2)]. A first fraction of 2.61 g of 2-propylamino-4-amino-6-chloropyrimidine (yield=48%; M.p.=92°–94° C. in a capillary) is obtained, followed by a second fraction of 1.2 g of 2-methylsulfonyl-4-amino-6-propylaminopyrimidine (yield=18%; M.p.=100°–102° C.).

2-Propylamino-4-amino-6-chloropyrimidine

Elemental analysis for C₇H₁₁N₄Cl; M = 186.64

|  | C | H | N | Cl |
|---|---|---|---|---|
| Calculated | 45.04 | 5.95 | 30.02 | 18.99 |
| Found | 44.95 | 6.02 | 30.00 | 18.89 |

The ¹H NMR and mass spectra are consistent with the expected structure.

2-Methylsulfonyl-4-amino-6-chloropyrimidine

Elemental analysis for C₈H₁₄N₄O₂S; M = 230.29

|  | C | H | N | O | S |
|---|---|---|---|---|---|
| Calculated | 41.73 | 6.13 | 24.33 | 13.90 | 13.92 |
| Found | 41.73 | 6.13 | 24.32 | 14.06 | 14.16 |

The ¹H NMR and mass spectra are consistent with the expected structure.

Stage 3
2-n-Propylamino-4-amino-6-chloropyrimidine 3-oxide

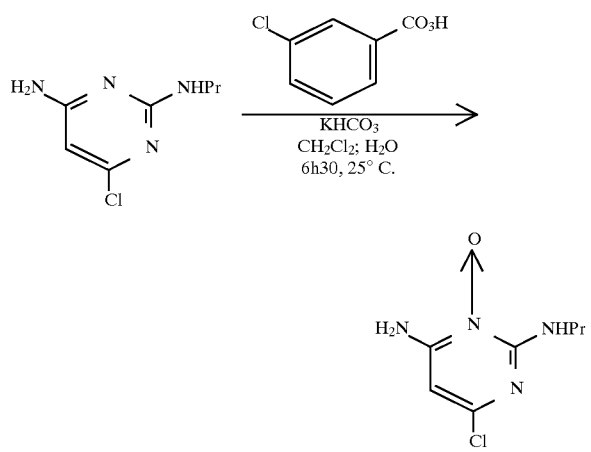

Procedure 1.56 g of KHCO₃ in solution in 20 ml of water and 1.22 g of 2-n-propylamino-4-amino-6-chloropyrimidine in solution in 20 ml of dichloromethane are introduced into a 100-ml three-necked flask. The two-phase mixture is cooled to about +10° C. and 4.1 g of 55% m-chloroperbenzoic acid are added portionwise. The mixture is allowed to return to room temperature. After 6 h 30 minutes' reaction the dichloromethane is evaporated off and the aqueous phase is acidified with 1.83 ml of 37% hydrochloric acid. The m-chlorobenzoic acid which precipitates is filtered off and the filtrate is then alkalified with 2.21 ml of 10N sodium hydroxide. This alkaline phase is extracted with 4×50 ml of butanol.

The butanol phases are combined and the solvent is evaporated off. A viscous liquid is obtained which is crystallized from 25 ml of diethyl ether. After filtration, 0.83 g of crude 2-n-propylamino-4-amino-6-chloro-pyrimidine 3-oxide are collected.

Crude yield=63%.

The ¹H NMR and mass spectra are consistent with the expected structure.

Stage 4
2-n-Propylamino-4-amino-6-N,N-dimthylaminopyrimidine 3-oxide

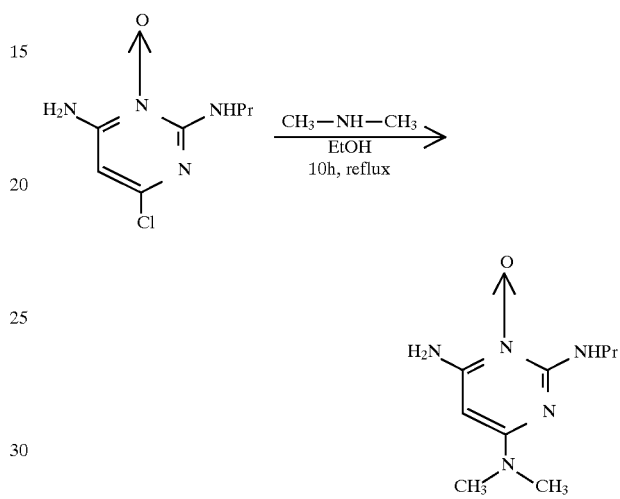

Procedure 0.39 g of 2-n-propylamino-4-amino-6-chloropyrimidine 3-oxide in solution in 20 ml of ethanol and 17 ml of an ethanolic solution containing 33% of N,N-dimethyl-amine are introduced into a 100-ml round bottom flask. The mixture is refluxed for 10 hours. The solvent is evaporated off and the crude product obtained is chromatographed on a silica column (eluent: CH₂Cl₂/CH₃OH=92/8). 0.25 g of 2-n-propylamino-4-amino-6-N,N-dimethyl-aminopyrimidine 3-oxide are collected.

Yield=62%.

The ¹H NMR and mass spectra are consistent with the expected structure.

Example 5
Synthesis of 2-amino-4-methylamino-6-pyrrolidinopyrimidine 3-oxide

Stage 1
2-Amino-4-methylamino-6-chloropyrimidine

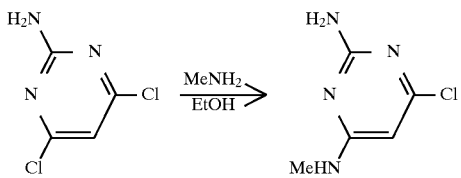

10 g of 2-amino-4,6-dichloropyrimidine are suspended in 100 ml of ethanol. 11.80 g of methylamine are added as a 40% solution in water. The reaction mixture is refluxed for 3 hours. After it has returned to room temperature, 4 g of potassium hydroxide in solution in 40 ml of ethanol are added. After being stirred for half an hour the reaction mixture is filtered on paper. It is evaporated to dryness. The precipitate obtained is taken up in 25 ml of water, filtered off on sintered glass, rinsed with 25 ml of water and then dried in vacuum and over phosphorus pentoxide. 8.50 g of 2-amino-4-methylamino-6-chloropyrimidine are obtained.

Yield=88%

ANALYSES

Mass spectrum consistent
$^1$H NMR spectrum consistent.

Stage 2
2-Amino-4-methylamino-6-chloropyrimidine 3-oxide

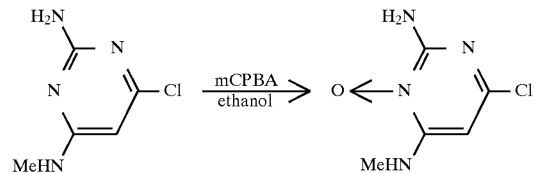

4 g of 2-amino-4-methylamino-6-chloropyrimidine are suspended in 50 ml of ethanol. After having cooled to 10° C., 11.9 g of meta-chloroperbenzoic acid are added dropwise as a solution in 100 ml of ethanol. At the end of addition, room temperature is regained and stirring is continued for 3 hours. The reaction mixture is cooled to 5° C. and then filtered on sintered glass. The precipitate obtained is recrystallized from 160 ml of a ⅔-⅓ ethanol-water mixture. 1.60 g of 2-amino-4-methylamino-6-chloropyrimidine 3-oxide are obtained.

Yield=36%

ANALYSES $^1$H NMR spectrum consistent
Mass spectrum consistent.

Stage 3
2-Amino-4-methylamino-6-pyrrolidinopyrimidine 3-oxide

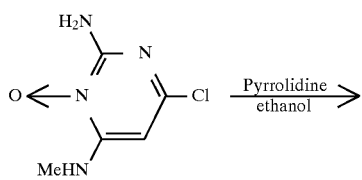

3.4 g of 2-amino-4-methylamino-6-chloropyrimidine 3-oxide are suspended in 70 ml of ethanol. 4.15 g of pyrrolidine are added. The reaction mixture is refluxed for 7 hours. After it has returned to room temperature, 1.30 g of potassium hydroxide are added as an 85% solution in 15 ml of ethanol. After 1 hour's stirring the mixture is filtered on paper. The filtrates are evaporated to dryness. The residue obtained is recrystallized from 50 ml of a 9/1 acetonitrile-water mixture. 2.40 g of 2-amino-4-methylamino-6-pyrrolidinopyrimidine 3-oxide are obtained.

Yield=56%

ANALYSES $^1$H NMR spectrum consistent
Mass spectrum consistent

| Elemental analysis for $C_9H_{15}N_5O$; M = 209 | | | | |
|---|---|---|---|---|
| | C | H | N | O |
| Calculated with 0.5 mole of water | 49.54 | 7.34 | 32.11 | 11.01 |
| Found | 49.54 | 7.22 | 32.15 | 11.30 |

Example 6
Synthesis of 2-amino-4-tert-butylamino-6-dimethylaminopyrimidine 3-oxide

Stage 1
2-Amino-4-tert-butylamino-6-chloropyrimidine

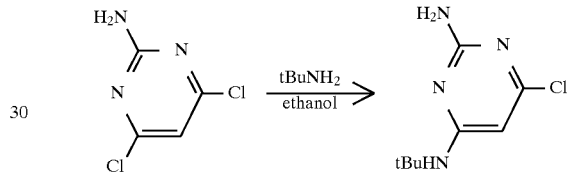

10 g of 2-amino-4,6-dichloropyrimidine are suspended in 100 ml of ethanol. 44.50 g of tert-butylamine are added. The reaction mixture is refluxed for 48 hours. It is evaporated to dryness. The residue is taken up in 50 ml of water. The mixture is stirred for 1 hour and the precipitate is then filtered off on sintered glass. It is recrystallized from 60 ml of a 50/50 ethanol-water mixture. 9.25 g of 2-amino-4-tert-butylamino-6-chloro-pyrimidine are obtained.

Yield=75%

ANALYSES $^1$H NMR spectrum consistent
Mass spectrum consistent

Stage 2
2-Amino-4-tert-butylamino-6-chloropyrimidine 3-oxide

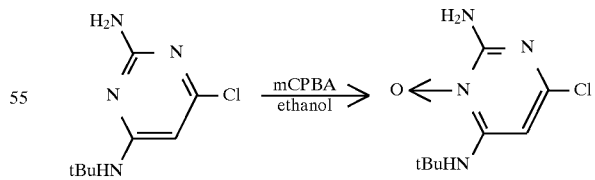

9 g of 2-amino-4-tert-butylamino-6-chloropyrimidine are suspended in 90 ml of ethanol. 24.70 g of meta-chloroperbenzoic acid are added dropwise as solution in 250 ml of ethanol. The reaction mixture is stirred at room temperature for 7 hours 30 minutes. It is evaporated to dryness. The residue is taken up in 100 ml of water. The pH is adjusted to 1 by adding concentrated hydrochloric acid. After 1 hour's stirring the precipitate is filtered off on sintered glass and then discarded. The filtrates are adjusted to pH 8 by adding concentrated sodium hydroxide and are then extracted with 3×100 ml of dichloromethane. The organic phase is separated off, dried over sodium sulfate, filtered on paper and evaporated to dryness. The residue obtained is recrystallized from 60 ml of acetonitrile. 1.30 g of 2-amino-4-tert-butylamino-6-chloropyrimidine 3-oxide are obtained.

Yield=14%

ANALYSES $^1$H NMR spectrum consistent

Mass spectrum consistent

Stage 3

2-Amino-4- tert-butylamino-6-dimethylaminopyrimidine 3-oxide

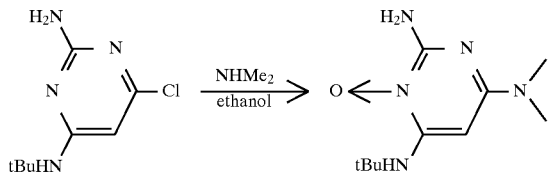

1.25 g of 2-amino-4-tert-butylamino-6-chloro-pyrimidine 3-oxide are suspended in 15 ml of ethanol. 5 ml of dimethylamine are added as 33% solution in ethanol. The reaction mixture is refluxed for 3 hours and then evaporated to dryness. The residue is taken up in 10 ml of water. The pH is adjusted to 8 by adding concentrated sodium hydroxide. The mixture is extracted with 3×20 ml of dichloromethane. The organic phase is dried over sodium sulfate, filtered on paper and evaporated to dryness. The precipitate obtained is recrystallized from 10 ml of acetonitrile. 520 mg of 2-amino-4-tert-butyl-amino-6-dimethylaminopyrimidine 3-oxide are obtained.

Yield=40%

ANALYSES $^1$H NMR spectrum consistent

Mass spectrum consistent

Elemental analysis for $C_{10}H_{19}N_5O$; M = 225

|  | C | H | N | O |
|---|---|---|---|---|
| Calculated | 53.33 | 8.45 | 31.11 | 7.11 |
| Found | 53.35 | 8.52 | 31.22 | 7.17 |

Example 7
Synthesis of 2,4-N,N'-diethylamino-6-dimethylaminopyrimidine 3-oxide

Stage 1
2.4-N,N'-Diethylamino-6-chloropyrimidine

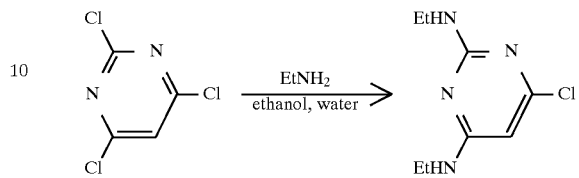

15 g of 2,4,6-trichloropyrimidine are dissolved in 150 ml of ethanol. 78 g of ethylamine are added drop-wise as 33% solution in water. The reaction mixture is refluxed for 7 hours. The ethanol is evaporated off. The residue is extracted with 3×100 ml of dichloromethane. The organic phase is washed with 100 ml of water, dried over sodium sulfate and evaporated to dryness. 15.90 g of 2,4-N,N'-diethylaminopyrimidine are obtained.

Yield=97%

ANALYSES $^1$H NMR spectrum consistent

Mass spectrum consistent

Elemental analysis for $C_8H_{13}N_4Cl$; M = 200.5

|  | C | H | N | Cl |
|---|---|---|---|---|
| Calculated | 47.88 | 6.48 | 27.93 | 17.70 |
| Found | 47.76 | 6.57 | 27.69 | 17.90 |

Stage 2
2.4-N,N'-Diethylamino-6-chloropyrimidine 3-oxide

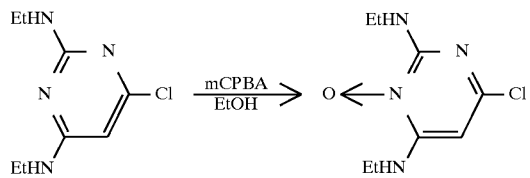

12 g of 2,4-N,N'-diethylamino-6-chloropyrimidine are dissolved in 50 ml of ethanol. The reaction mixture is cooled to 10° C. 32.9 g of meta-chloroperbenzoic acid are added dropwise as solution in 180 ml of ethanol. After 24 hours' stirring at room temperature 200 ml of water are added. The ethanol is evaporated off. The pH of the resulting aqueous phase is adjusted to 1 by adding concentrated hydrochloric acid. The reaction mixture is stirred for 1 hour, filtered on sintered glass and then rinsed with 50 ml of water. The precipitate is removed. The filtrates are adjusted to pH 8 by addition of sodium hydroxide and are then extracted with 3×100 ml of dichloromethane. The organic phase is dried over sodium sulfate and evaporated to dryness. The residue is purified by chromatography on a silica column (eluent: ethyl acetate/methanol). 2.2 g of 2,4-N,N'-diethylamino-6-chloropyrimidine 3-oxide are obtained.

Yield=17%

ANALYSES

Mass spectrum consistent
$^1$H NMR spectrum consistent

Stage 3

2.4-N,N'-Diethylamino-6-dimethylaminopyrimidine 3-oxide

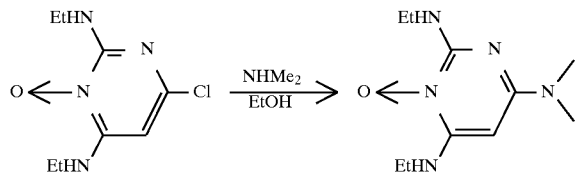

2.20 g of 2,4-N,N'-diethylamino-6-chloropyrimidine 3-oxide are dissolved in 20 ml of ethanol. 10 ml of dimethylamine are added as 33% solution in ethanol. The reaction mixture is refluxed for 5 hours and then evaporated to dryness. The residue is taken up in 25 ml of water. The pH is adjusted to 8 by adding concentrated sodium hydroxide and the mixture is then extracted with 4×25 ml of ethyl acetate. The organic phase is dried over sodium sulfate, filtered on paper, and evaporated to dryness. The solid is recrystallized from 40 ml of isopropyl ether. 750 mg of 2,4-N,N'-diethylamino-6-dimethylaminopyrimidine 3-oxide are obtained.

Yield=33%

ANALYSES

Mass spectrum consistent
$^1$H NMR spectrum consistent

| Elemental analysis for $C_{10}H_{19}N_5O$; M = 225 | | | | |
| --- | --- | --- | --- | --- |
|  | C | H | N | O |
| Calculated | 53.33 | 8.44 | 31.11 | 7.11 |
| Found | 53.20 | 8.44 | 31.13 | 7.24 |

Example 8

Synthesis of 2-amino-4-propylamino-6-piperidinopyrimidine 3-oxide

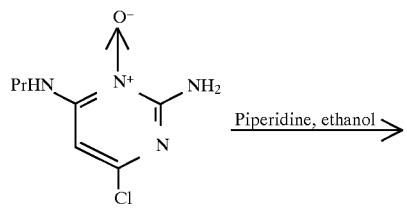

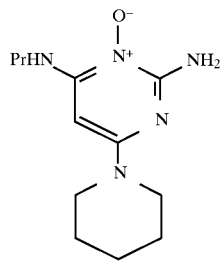

2 g of 2-amino-4-propylamino-6-chloropyrimidine 3-oxide, prepared according to the first two stages of the process of Example 1, are suspended in 20 ml of ethanol. 1.75 g of piperidine are added. The reaction mixture is refluxed for 19 hours. After it has returned to room temperature, 660 mg of potassium hydroxide are added as a solution in 10 ml of ethanol. After 1 hour's stirring the mixture is filtered on paper. The filtrates are evaporated to dryness. The residue is recrystallized from 25 ml of acetone. 950 mg of 2-amino-4-propylamino-6-piperidinopyrimidine 3-oxide are obtained.

Yield=38%

ANALYSES

Mass spectrum consistent
$^1$H NMR spectrum consistent

| Elemental analysis for $C_{12}H_{21}N_5O$; M = 251 | | | | |
| --- | --- | --- | --- | --- |
|  | C | H | N | O |
| Calculated | 57.37 | 8.37 | 27.89 | 6.37 |
| Found | 57.44 | 8.42 | 27.88 | 6.21 |

Example 9

Synthesis of 2-amino-5-butylamino-6-diethylaminopyrimidine 3-oxide

Stage 1

2-Amino-4-butylamino-6-chloropyrimidine

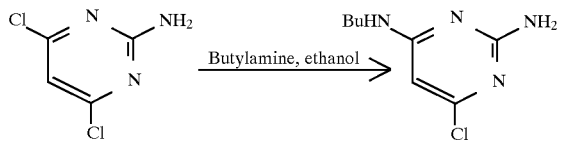

10 g of 2-amino-4,6-dichloropyrimidine are suspended in 100 ml of ethanol. 11.15 g of butylamine are added. The reaction mixture is refluxed for 2 hours and then evaporated to dryness. The residue is taken up in 100 ml of water. After 1 hour's stirring the precipitate is filtered off on sintered glass and is then recrystallized from 80 ml of 6/4 water/acetonitrile. 8.75 g of 2-amino-4-butylamino-6-chloropyrimidine are obtained.

Yield=71%

ANALYSES

Mass spectrum consistent
¹H NMR spectrum consistent

| Elemental analysis for $C_8H_{13}N_4Cl$; M = 200.5 | | | | |
|---|---|---|---|---|
| | C | H | N | Cl |
| Calculated | 47.88 | 6.48 | 27.93 | 17.70 |
| Found | 47.63 | 6.60 | 27.88 | 17.78 |

Stage 2

2-Amino-4-butylamino-6-chloropyrimidine 3-oxide

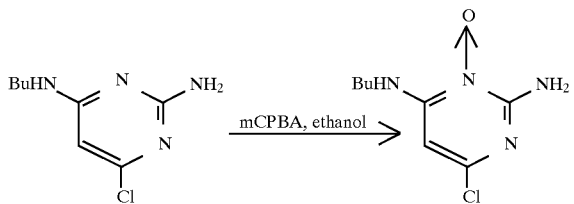

8.5 g of 2-amino-4-butylamino-6-chloropyrimidine are dissolved in 150 ml of ethanol. 19.95 g of meta-chloroperbenzoic acid are added dropwise as solution in 150 ml of ethanol. The reaction mixture is stirred at room temperature for 2 hours. 250 ml of water are added and ethanol is then evaporated off. The pH is adjusted to 1 with concentrated hydrochloric acid. After 1 hour's stirring, the precipitate is filtered off on sintered glass, rinsed with 50 ml of water and discarded. The pH of the solution is adjusted to 8 by adding sodium hydroxide. The mixture is extracted with 3×100 ml of dichloromethane. The organic phase is dried over sodium sulfate and then evaporated to dryness. The precipitate obtained is recrystallized from 50 ml of acetonitrile. 2.35 g of 2-amino-4-butylamino-6-chloropyrimidine 3-oxide are obtained.

Yield=26%

ANALYSES

Mass spectrum consistent
¹H NMR spectrum consistent

| Elemental analysis for $C_8H_{13}N_4OCl$; M = 216.5 | | | | | |
|---|---|---|---|---|---|
| | C | H | N | O | Cl |
| Calculated | 44.34 | 6.00 | 25.87 | 7.39 | 16.40 |
| Found | 44.28 | 6.08 | 25.74 | 7.40 | 16.32 |

Stage 3

2-Amino-4-butylamino-6-dimethylaminopyrimidine 3-oxide

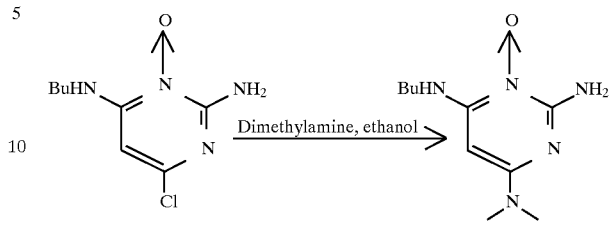

1.5 g of 2-amino-4-butylamino-6-chloropyrimidine 3-oxide are placed in 10 ml of ethanol. 5 ml of dimethylamine are added as 33% solution in ethanol. The reaction mixture is refluxed for 4 hours and is then evaporated to dryness. The precipitate obtained is taken up in 20 ml of water. The pH is adjusted to 8 by adding sodium hydroxide. The mixture is extracted with 3×50 ml of butanol. The butanol phase is evaporated to dryness. The precipitate is recrystallized from 10 ml of acetonitrile. 610 mg of 2-amino-4-butylamino-6-dimethylaminopyrimidine 3-oxide are obtained.

Yield=39%

ANALYSES

Mass spectrum consistent
¹H NMR spectrum consistent

| Elemental analysis for $C_{10}H_{19}N_5O$; M = 225 | | | | |
|---|---|---|---|---|
| | C | H | N | O |
| Calculated | 53.33 | 8.44 | 31.11 | 7.11 |
| Found | 53.50 | 8.50 | 31.11 | 7.30 |

Example 10

Synthesis of 2-amino-4-ethylamino-6-dimethylminopyridine 3-oxide

Stage 1

2-Amino-4-ethylamino-6-chloropyrimidine

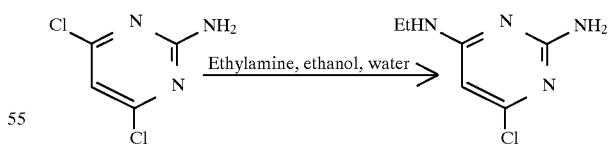

10 g of 2-amino-4,6-dichloropyrimidine are suspended in 100 ml of ethanol. 20.8 g of ethylamine are added as 33% solution in water. The reaction mixture is refluxed for 2 hours and is then evaporated to dryness. The precipitate obtained is taken up in 100 ml of water. After 1 hour's stirring, the mixture is filtered on sintered glass. The precipitate is recrystallized from 25 ml of acetonitrile. 8.10 g of 2-amino-4-ethylamino-6-chloropyrimidine are obtained.

Yield=77%

ANALYSES

Mass spectrum consistent
¹H NMR spectrum consistent

Elemental analysis for C₆H₉N₄Cl; M = 172.5

|  | C | H | N | Cl |
|---|---|---|---|---|
| Calculated | 41.74 | 5.22 | 32.46 | 20.58 |
| Found | 41.81 | 5.28 | 32.56 | 20.50 |

Stage 2
2-Amino-4-ethylamino-6-chloropyrimidine 3-oxide

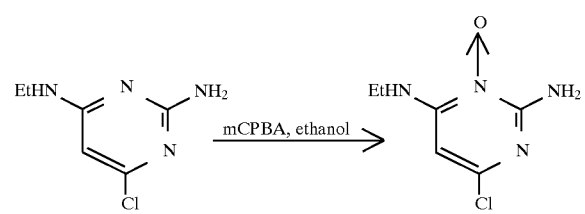

8 g of 2-amino-4-ethylamino-6-chloropyrimidine are suspended in 150 ml of ethanol. 21.80 g of meta-chloroperbenzoic acid are added dropwise as solution in 150 ml of ethanol. After 2 hours' stirring, the reaction mixture is concentrated to a third in a rotary evaporator. The precipitate is filtered off on sintered glass, washed with 2×50 ml of ethyl ether and is then recrystallized from 60 ml of a 9/1 acetonitrile-ethanol mixture. 3.05 g of 2-amino-4-ethylamino-6-chloropyrimidine 3-oxide are obtained.

Yield=35%

ANALYSES

Mass spectrum consistent
¹H NMR spectrum consistent

Stage 3
2-Amino-4-ethylamino-6-dimethylaminopyrimidine 3-oxide

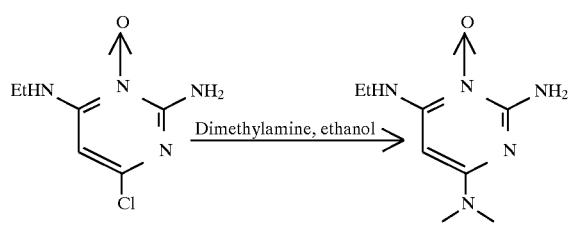

3 g of 2-amino-4-ethylamino-6-chloropyrimidine 3-oxide are placed in 20 ml of ethanol. 10 ml of dimethyl-amine are added as 33% solution in ethanol. The reaction mixture is refluxed for 4 hours and is then evaporated to dryness. The residue is taken up in 25 ml of water and the pH is then adjusted to 8 by adding sodium hydroxide. The mixture is extracted with 4×50 ml of dichloro-methane. The organic phase is dried over sodium sulfate, filtered on paper and evaporated to dryness. The precipitate is recrystallized from 26 ml of a 95.75/4.25 acetonitrile-water mixture. 1.20 g of 2-amino-4-ethyl-amino-6-dimethylaminopyrimidine 3-oxide are obtained.

Yield=38%

ANALYSES

Mass spectrum consistent
¹H NMR spectrum consistent

Elemental analysis for C₈H₁₅N₅O; M = 197

|  | C | H | N | O |
|---|---|---|---|---|
| Calculated | 48.73 | 7.61 | 35.53 | 8.12 |
| Found | 48.79 | 7.64 | 35.52 | 8.29 |

Example 11
Synthesis of 2-amino-4-propylamino-5-chloro-6-dimethylaminopyrimidine 3-oxide

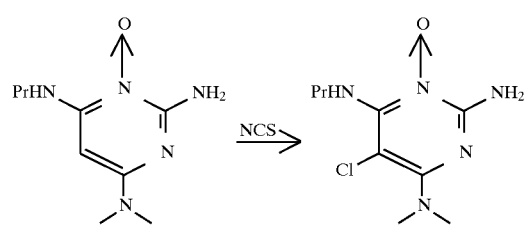

1 g of 2-amino-4-propylamino-6-dimethylaminopyrimidine 3-oxide of Example 1 is dissolved in 15 ml of ethanol. 0.75 g of N-chlorosuccinimide are added as solution in 35 ml of ethanol, dropwise at room temperature. After 4 hours' stirring the reaction mixture is evaporated to dryness. The oil obtained is taken up in 10 ml of water. The pH is adjusted to 8 by adding sodium hydroxide and the mixture is then extracted with 3×20 ml of butanol. The butanol phase is evaporated to dryness. The residue is recrystallized from 5 ml of acetonitrile. 0.7 g of 2-amino-4-propylamino-5-chloro-6-dimethylaminopyrimidine 3-oxide are obtained.

Yield=60%

ANALYSES

Mass spectrum consistent
¹H NMR spectrum consistent

Elemental analysis for C₉H₁₆N₅OCl; M = 245.5

|  | C | H | N | O | Cl |
|---|---|---|---|---|---|
| Calculated | 43.99 | 6.52 | 28.51 | 6.52 | 14.46 |
| Found | 44.19 | 6.54 | 28.46 | 6.76 | 14.36 |

EXAMPLES OF FORMULATION

Example 1

The following composition is prepared:

| 2-amino-4-propylamino-6-dimethylamino-pyrimidine 3-oxide | 3.0 g |
|---|---|
| 95° ethanol | 30.0 g |
| water | q.s. 100.0 g |

This composition takes the form of a lotion.

Example 2

The following composition is prepared:

| | |
|---|---|
| 4-amino-2-propylamino-6-dimethylamino-pyrimidine 3-oxide | 2.0 g |
| propylene glycol | 20.0 g |
| ethanol | 30.0 g |
| water | q.s. 100.0 g |

This composition takes the form of a lotion.

1 to 2 ml of these lotions are applied to the alopecic regions of the scalp, once or twice daily during 4 months' treatment.

What is claimed is:

1. In a process for slowing down the loss of hair and for inducing and stimulating its growth, the improvement which consists in applying to the hair and scalp an effective amount of a composition which consists essentially of, in a physiologically acceptable medium selected from the group consisting of water, lower alcohols having from 1 to 4 carbon atoms, alkylene glycols, alkyl ethers of alkylene glycols, and mixtures thereof, at least one compound of formula:

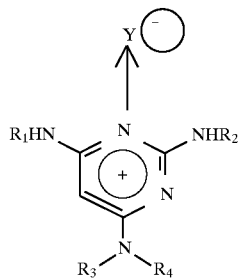

in which:
R$_1$ and R$_2$, independently of each other, denote a hydrogen atom or a C$_1$–C$_8$ alkyl radical, with the proviso that R$_1$ and R$_2$ do not simultaneously denote a hydrogen atom;
R$_3$ and R$_4$, independently of each other, denote a hydrogen atom or a C$_1$–C$_8$ alkyl radical, with the proviso that R$_3$ and R$_4$ taken together with the nitrogen atom attached to position 6 of the pyrimidine ring form a heterocyclic moiety having from 3 to 6 carbon atoms;
X denotes a hydrogen atom or a halogen;
Y denotes O or OSO$_3$;
and its addition salts of physiologically acceptable acids, and other hair or scalp treating active ingredients, in order to have no antihypertensive effect or a substantially reduced antihypertensive effect in comparison to minoxidil.

2. The process as claimed in claim 1, wherein in formula (I) the C$_1$–C$_8$ alkyl radicals are selected from the group consisting of methyl, ethyl, n-propyl, isopropyl, n-butyl, tert-butyl, hexyl, octyl and 2-ethylhexyl; the halogen atom is chlorine or bromine; and the heterocyclic moiety is selected from the group consisting of morpholino, piperidino, pyrrolidino, piperazino and N-4'-alkylpiperazino in which the alkyl group in position 4' contains from 1 to 6 carbon atoms.

3. The process as claimed in claim 1, wherein the compound of formula (I) is 2-amino-4-propylamino-6-dimethylaminopyrimidine 3-oxide or one of its addition salts of physiologically acceptable acids.

4. The process as claimed in claim 1, in which the composition is in the form of an ointment, tincture, cream, pomade, powder, plaster, saturated pad, solution, emulsion, vesicular dispersion, lotion, gel, spray or anhydrous or aqueous suspension suitable for pharmaceutical application.

5. The process as claimed in claim 1, wherein the compound of formula (I) is present in concentrations of between 0.1 and 10% by weight relative to the total weight of the composition.

6. The process as claimed in claim 1, in which the composition is in the form of lotion, gel, soap, shampoo, aerosol or foam and contains at least one compound of formula (I) in a concentration of between 0.01 and 5% by weight.

7. The process as claimed in claim 1, in which the composition further comprises a hydrating agent and an antiseborrheic agent.

8. The process as claimed in claim 1, in which the composition further comprises at least one agent which improves the activity of the compounds of formula (I) with respect to the regrowth and/or slowing down of the loss of hair.

9. The process as claimed in claim 8, wherein said agent which improves the activity of the regrowth and/or slowing down of hair loss is selected from the group consisting of nicotinic acid esters, steroidal and nonsteroidal antiinflammatory agents, retinoids, antibacterial agents, calcium antagonistic agents, hormones, antiandrogenic agents, OH radical scavengers, esterified oligosaccharides, hexasaccharic acid derivatives, glycosidase inhibitors, glycosaminoglycanase and proteoglycanase inhibitors and tyrosine kinase inhibitors.

10. The process as claimed in claim 1, in which the composition further comprises at least one compound selected from the group consisting of diazoxide, spiroxazone, phospholipids, linoleic and linolenic acids, and salicylic acid, hydroxycarboxylic and ketocarboxylic acids, their esters, lactones and their corresponding salts, anthralin, carotenoids and 5,8,11,14-eicosatetraynoic and 5,8,11-eicosatriynoic acids, their esters and amides.

11. The process as claimed in claim 1, in which the composition further comprises a surface-active agent selected from the group consisting of nonionic and amphoteric surface-active agents.

12. The composition as claimed in claim 7, wherein the physiologically acceptable medium is thickened by means of thickening and/or gelling agents and contains preserving agents, stabilizers, pH regulators, osmotic pressure modifiers, emulsifiers, UV-A and UV-B filters and antioxidants.

13. In a process for slowing down the loss of hair and for inducing and stimulating hair growth, the improvement which consists in applying to the hair and scalp an effective amount of a composition which consists essentially of, in a physiologically acceptable medium selected from the group consisting of water, lower alcohols having from 1 to 4 carbon atoms, alkylene glycols, alkyl ethers of alkylene glycols and mixtures thereof, at least one compound of formula

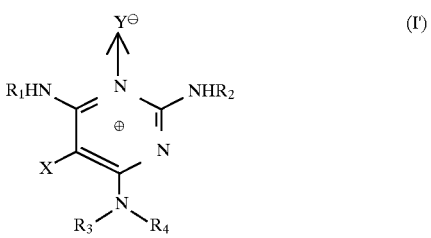

in which:
X denotes a hydrogen or halogen atom;

Y denotes O or $OSO_3$;

$R_1$ and $R_2$, independently of one another, denote a $C_1$–$C_8$ alkyl radical;

$R_3$ and $R_4$, independently of each other, denote a hydrogen atom or a $C_1$–$C_8$ alkyl radical, with the proviso that $R_3$ and $R_4$ do not simultaneously denote a hydrogen atom, or $R_3$ and $R_4$ taken together with the nitrogen attached to position 6 of the pyrimidine ring form a heterocyclic moiety having from 3 to 6 carbon atoms; and their addition salts of physiologically acceptable acids, and other hair or scalp treating active ingredients, in order to have no antihypertensive effect or a substantially reduced antihypertensive effect in comparison to minoxidil.

* * * * *